United States Patent [19]

Grätzel et al.

[11] Patent Number: 5,393,903
[45] Date of Patent: Feb. 28, 1995

US005393903A

[54] MONO, BIS OR TRIS(SUBSTITUTED 2,2'-BIPYRIDINE) IRON, RUTHENIUM, OSMIUM OR VANADIUM COMPLEXES AND THEIR METHODS OF PREPARATION

[75] Inventors: Michael Grätzel, St-Sulpice; David Fraser, Vevey; Shaik M. Zakeeruddin, Renens; Mohammed K. Nazeeruddin, Chavannes, all of Switzerland

[73] Assignee: Asulab S.A., Bienne, Switzerland

[21] Appl. No.: 949,485

[22] PCT Filed: Feb. 19, 1992

[86] PCT No.: PCT/CH92/00033

§ 371 Date: Oct. 19, 1992

§ 102(e) Date: Oct. 19, 1992

[87] PCT Pub. No.: WO92/14741

PCT Pub. Date: Sep. 3, 1992

[30] Foreign Application Priority Data

Feb. 21, 1991 [FR] France ................ 91 02199

[51] Int. Cl.$^6$ .............. C07F 15/00; C07F 15/02; C07F 19/00; C09K 3/00
[52] U.S. Cl. .................. 556/137; 556/42; 556/43; 556/44; 556/138; 556/140; 556/146; 106/287.18
[58] Field of Search ............ 546/10; 556/43, 137, 556/138, 140, 146, 42, 44; 106/287.18

[56] References Cited

U.S. PATENT DOCUMENTS 4,545,382 10/1985 Higgins et al. ............ 128/635
4,745,076 5/1988 Muller et al. ............ 436/537
5,075,447 12/1991 Muller et al. ............ 546/10

FOREIGN PATENT DOCUMENTS 0074807 3/1983 European Pat. Off. .
0178450 4/1986 European Pat. Off. .
956242 4/1964 United Kingdom .
8602734 5/1986 WIPO .
9005732 5/1990 WIPO .

OTHER PUBLICATIONS

GB, A, 95642 (The Australian National University) 22 Apr. 1984.

Organic Magnetic Resonance, vol. 22, No. 6, Jun. 1984, M. J. Cook et al.: "Luminescent metal complexes 4+ − 13C NMR spectra of the tris chelates of substituted 2,2'-bipyridyls and 1,10-phenanthrolines with ruthenium(II) and osmium(II)", pp. 388–394.

Chemical Abstracts, vol. 113, 1990, (Columbus, Ohio, US), L. Della Ciana et al.: "Synthesis and characterzation of a new family of luminescent cis-(4,4'-X2-5,-5'-Y2-2,2'-bipyridine)20s(CO)CI(PF6) complexes (X=NEt2, OMe, Me, H, CL, Y=H; X=H, Y=Me; X=Y=Me): control of excited-state properties by bipridyl substituents", p. 814, No. 90292a, & INORG. CHEM. 1990, 29(15), 2792-8.

Chemical Abstracts, vol. 101, 1984, (Columbus, Ohio, US), K. J. Takeuchi et al.: "Redox and spectral properties of monooxo polypyridyl complexes of ruthenium and osmium in aqueous media", p. 574, No. 16171w, & INORG. CHEM. 1984, 23(13), 1845-51.

Journal of the Chemical Society Perkin Transactions II, vol. 8, 1984, M. J. Cook et al.: "Luminescent metal complexes. Part 1. Tris-chelates of substituted 2,2'-bipyridyls with ruthenium(II) as dyes for luminescent solar collectors", pp. 1293–1301.

(List continued on next page.)

Primary Examiner—Raymond J. Henley, III
Assistant Examiner—Phyllis G. Spivack

[57] ABSTRACT

Mono, bis and tris(substituted 2,2'-bipyridine) complexes of iron, ruthenium, osmium or vanadium are described wherein the bipyridine is substituted by a hydroxy or alkoxy group, or a primary, secondary or tertiary amine group.

24 Claims, No Drawings

OTHER PUBLICATIONS

Journal of the Chemical Society Perkin Transactions II, vol. 8, 1984, M. J. Cook et al.: "Luminescent metal complexes. Part 2. A model for the luminescence properties of the tris-chelates of substituted 2,2'-bipyridyls with ruthenium (II)", pp. 1303–1307, see the whole article.

Chemical Abstracts, vol. 100, 1984, (Columbus, Ohio (US), E. C. Constable: "Nucleophilic attack upon coordinated heterocycles definitive evidence for the enhanced electrophilicity of coordinated pyridines", see p. 701, abstract No. 150011b, & INORG. CHIM. ACTA 1984, 82(1), 53–7, see the whole article.

Journal of the Chemical Society, Chemical Communications, No. 13, 1988, M. K. Nazeerudin et al.: "Spontaneous oxidation of water to oxygen by the mixed-valence mu-oxo ruthenium dimer L2(H20)RuIII-–O–RuIV(OH)L2 (L=2,2'-bipyridyl-5,5'-dicarboxylic acid)", pp. 872–874, see the whole article.

Gopinathan et al., Indian Journal of Chemistry. vol. 25A, Nov. 1986, pp. 1015–1017.

Araki et al., Bull. Chem. Soc. Japan. 63(5), 1990, pp. 1299–1304.

MONO, BIS OR TRIS(SUBSTITUTED 2,2'-BIPYRIDINE) IRON, RUTHENIUM, OSMIUM OR VANADIUM COMPLEXES AND THEIR METHODS OF PREPARATION

TECHNICAL FIELD

The instant invention relates to a new family of mono, bis or tris(substituted 2,2'-bipyridine) iron, ruthenium, osmium or vanadium complexes, the bipyridine being substituted by at least one electron donor group. This invention also relates to methods for the preparation of these complexes.

BACKGROUND OF THE INVENTION

Determination of the concentration of certain components, especially glucose in biological fluids, has been considerably improved by the use of amperometric sensors using an electrode coated with a mediator and with an enzyme specific to said component, for example glucose oxidase, for the detection of glucose. These sensors thus make it possible to measure the transfer of electrons passing between the enzyme and the electrode by the intermediary of the mediator, this electron transfer being proportional to the amount-of component present in the sample of the biological fluid to be tested.

The quality of these sensors, i.e., their accuracy, the reproducibility of the results given by several sensors of the same series, their reliability and the speed of their response time largely depends upon the mediator used.

Mediators known to date, for example from U.S. Pat. No. 4,545,382 of Genetics International, include polyviologen, chloranil, fluoranil or ferrocene.

These mediators have, however, a certain number of disadvantages.

Because they do not transfer the electrons between the enzyme and the electrode sufficiently quickly, the response time of the sensor is rather long. In addition, some of these mediators, such as ferrocene, are relatively volatile or unstable, particularly when exposed to light and the sensors have to be stored under rather strict lighting and temperature conditions. In addition some mediators, especially ferrocene, decompose in water by hydrolysis which is a disadvantage when the sensors are used in blood.

Finally, oxygen enters into competition with some of these mediators and the results of glucose concentration measurements vary according to the amount of oxygen present in the blood. This can be a disadvantage depending on whether venous or arterial blood is being examined.

DISCLOSURE OF THE INVENTION

It was consequently desirable to seek and prepare mediators that are fast, stable and do not have interference problems with oxygen.

This search for mediators has led to the preparation of a new family of mono, bis or tris(substituted 2,2'-bipyridine) complexes of iron, ruthenium, osmium or vanadium, the bipyridine being substituted by at least one electron donor group.

This new family of complexes is not only of theoretical interest, but also above all because of these good mediator properties and the many other practical applications which it could have.

The invention will be better understood from a study of the following description of the family of complexes and of various embodiments of the processes for preparing these complexes.

The new family of mono, bis or tris(substituted 2,2'-bipyridine) complexes of a metal M has the following general formula (I):

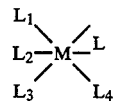

in which M is iron, osmium, ruthenium or vanadium.

L represents a bipyridine substituted by at least one electron donor group, conferring on the complex the oxidation-reduction properties desirable for a mediator.

A preferred complex of the metal M has the following general formula (I):

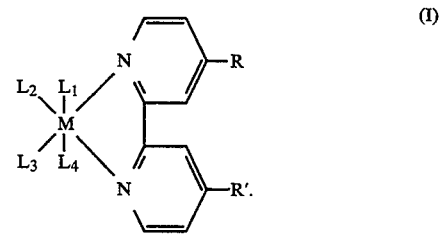

in which R and R' are the same and each is a hydroxy, alkoxy or aryloxy group or a primary, secondary or tertiary amine group.

$L_1$, $L_2$, $L_3$, $L_4$ are ligands forming a coordination complex with iron, osmium, ruthenium or vanadium.

It will also be noted that in these complexes, the ligand L preferably represents a bipyridine disubstituted in the 4,4'-positions and more particularly 4,4'-dihydroxy-2,2'-bipyridine, 4,4'-dimethoxy-2,2'-bipyridine or 4,4'-bis(N,N-ethyl amino)-2,2'-bipyridine also known as 4,4'-bis(N,N -diethylamino)-2,2'-bipyridine, the complexes then having the following general formulae referenced (II), (III) and (IV) respectively:

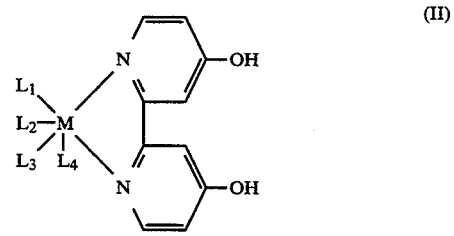

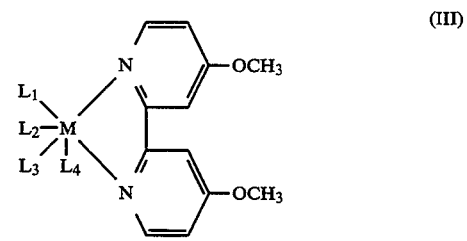

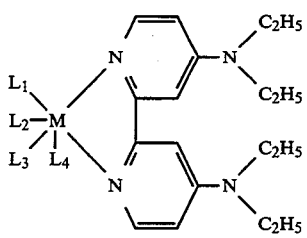

(IV)

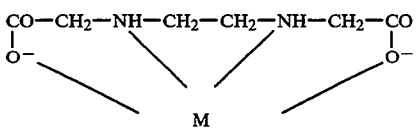

The ligands $L_1$, $L_2$, $L_3$ and $L_4$ are mono-, di-, ter- or tetradentate and may be combined in the following manner:

- either $L_1$, $L_2$, $L_3$ and $L_4$ each represents a monodentate ligand and are wholly or partially the same or different from one another,
- or $L_1$ and $L_2$ together are a bidentate ligand and $L_3$ and $L_4$ are the same or different and each represents a monodentate ligand,
- or $L_1$ and $L_2$ on the one hand and $L_3$ and $L_4$ on the other hand form respectively a bidentate ligand,
- or $L_1$ represents a monodentate ligand and $L_2$, $L_3$ and $L_4$ together form a terdentate ligand,
- or $L_1$, $L_2$, $L_3$ and $L_4$ together form a tetradentate ligand.

Monodentate ligands that can be used include: $CN^-$, $Cl^-$, $Br^-$, $I^-$, $SCN^-$, $H_2O$, $NH_3$, triphenylphosphine, trialkylphosphines, primary, secondary or tertiary amines, pyridine or pyridines substituted by $Cl$, $NH_2$, $NO_2$ or by an alkyl group.

Bidentate ligands that may be used include: ethylenediamine, 1,2 bis(2-pyridyl)ethane, oxalic acid $O^- \text{—CO—CO—} O^-$, acetylacetone $CH_3\text{—CO—CH}_2\text{—CO—CH}_3$, glycine $NH_2\text{—CH}_2\text{—COO}^-$ and, preferably, a bipyridine or phenanthroline disubstituted by an $R_1$ group and an $R_2$ group, $R_1$ and $R_2$ being the same or different and each representing hydrogen, $NO_2$, $Cl$, an alkyl group, an aryl group, an OH group, an alkoxy group, an aryloxy group or a primary, secondary or tertiary amine group.

The terdentate ligand preferably used is terpyridine of the general formula (V):

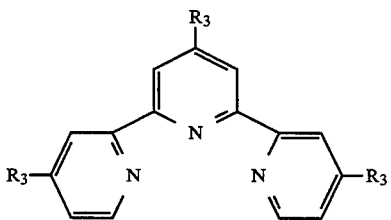

(V)

in which $R_3$ represents hydrogen or an alkyl group.

The tetradentate ligand preferably used is triethylenetetraamine:

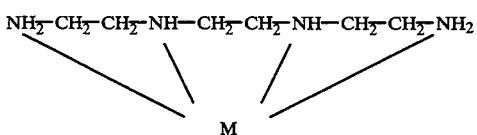

shown in the above diagram in coordination with the metal M, and ethylenediaminediacetic acid also shown in coordination with the metal M.

When $L_1$ and $L_2$ on the one hand and $L_3$ and $L_4$ on the other hand form respectively a bidentate ligand and when these two bidentate ligands are the same as the ligand L, a tris complex (ligand L) is obtained of a metal M which is iron, ruthenium, osmium or vanadium.

The preferred tris (ligand L) complexes of the present invention are:
- tris(4,4'-dihydroxy-2,2'-bipyridine) complexes of the metal M, and
- tris(4,4'-dimethoxy-2,2'-bipyridine) complexes of the metal M, and
- tris(4,4'-bis(N,N-ethylamino)-2,2'-bipyridine) complexes of the metal M.

When $L_1$ and $L_2$ together form a first bidentate ligand and when $L_3$ and $L_4$ together form a second bidentate ligand and when in addition only the first bidentate ligand is identical to the ligand L, a bis (ligand L) complex of the metal M is obtained, M being as defined above.

The preferred bis (ligand L) complexes of the instant invention are:
- bis(4,4'-dihydroxy-2,2'-bipyridine)mono(2,2'-bipyridine) complexes of the metal M,
- bis(4,4'-dihydroxy-2,2'-bipyridine)mono(4,4'-dimethoxy-2,2'-bipyridine) complexes of the metal M,
- bis(4,4'-dihydroxy-2,2'-bipyridine)mono(4,4'-dimethyl-2,2'-bipyridine) complexes of the metal M,
- bis(4,4'-dihydroxy-2,2'-bipyridine)mono(4-alkyl-2,2'-bipyridine) complexes of the metal M,
- bis(4,4'-dihydroxy-2,2'-bipyridine)mono(4,4'-dialkyl-2,2'-bipyridine) complexes of the metal M,
- bis(4,4'-dihydroxy-2,2'-bipyridine)mono(4,7-dihydroxy-1,10phenanthroline) complexes of the metal M,
- bis(4,4'-dihydroxy-2,2'-bipyridine) mono(4,4'-bis (N,N-ethylamino)-2,2'-bipyridine) complexes of the metal M,
- bis(4,4'-dimethoxy-2,2'-bipyridine)mono(2,2'-bipyridine complexes of the metal M,
- bis (4,4'-dimethoxy-2,2'-bipyridine)mono(4,4'-dimethyl-2,2'-bipyridine) complexes of the metal M,
- bis(4,4'-dimethoxy-2,2'-bipyridine)mono(4 -alkyl-2,2'-bipyridine) complexes of the metal M,
- bis (4,4'-dimethoxy-2,2'-bipyridine)mono(4,4'-dialkyl-2,2'-bipyridine) complexes of the metal M,
- bis (4,4'-dimethoxy-2,2'-bipyridine)mono(4,7-dihydroxy-1,10-phenanthroline) complexes of the metal M,
- bis(4,4'-dimethoxy-2,2'-bipyridine)mono(4,4'-dihydroxy-2,2'-bipyridine) complexes of the metal M,
- bis(4,4'-dimethoxy-2,2'-bipyridine)mono(4,4'-bis(N,N-ethylamino)-2,2'-bipyridine) complexes of the metal M,
- bis(4,4'-bis(N,N-ethylamino)-2,2'-bipyridine) mono(2,2'-bipyridine) complexes of the metal M,
- bis(4,4'-bis(N,N-ethylamino)-2,2'-bipyridine mono(4,4'-dimethoxy-2,2'-bipyridine) complexes of the metal M,
- bis(4,4'-bis(N,N-ethylamino)-2,2'-bipyridine mono(4,4'-dimethyl-2,2'-bipyridine) complexes of the metal M, bis(4,4'-bis(N,N-ethylamino)-2,2'-bipyridine mono(4-alkyl-2,2'-bipyridine) complexes of the metal M,
bis(4,4'-bis(N,N-ethylamino)-2,2'-bipyridine mono(4,4'-dialkyl-2,2'-bipyridine) complexes of the metal M,
bis(4,4'-bis(N,N-ethylamino)-2,2'-bipyridine mono((4,4'-dihydroxy-2,2'-bipyridine) complexes of the metal M,
bis(4,4'-bis(N,N-ethylamino)-2,2'-bipyridine mono((4,7-dihydroxy-1,10-phenanthroline) complexes of the metal M.

When $L_1$ and $L_2$ together form a first bidentate ligand and when $L_3$ and $L_4$ together form a second bidentate ligand and when in addition this first and this second ligand differ from the ligand L, a mono((ligand L) complex of a metal M which is iron, ruthenium, osmium or vanadium is obtained.

When this first ligand ($L_1$, $L_2$) and this second ligand ($L_3$, $L_4$) are identical, the preferred mono((ligand L) complexes of the instant invention are the following:
mono(4,4'-dihydroxy-2,2'-bipyridine)bis(4,4'-dimethyl-2,2'-bipyridine) complexes of the metal M,
mono(4,4'-dihydroxy-2,2'-bipyridine)bis(2,2'-bipyridine) complexes of the metal M,
mono(4,4'-dihydroxy-2,2'-bipyridine)bis(4 -alkyl-2,2'-bipyridine) complexes of the metal M,
mono(4,4'-dihydroxy-2,2'-bipyridine)bis(4,7-dihydroxy-1,10-phenanthroline) complexes of the metal M,
mono(4,4'-dimethoxy-2,2'-bipyridine)bis(4,4'-dimethyl-2,2'-bipyridine) complexes of the metal M,
mono(4,4'-dimethoxy-2,2'-bipyridine)bis(2,2'-bipyridine) complexes of the metal M,
mono(4,4'-dimethoxy-2,2'-bipyridine)bis(4-alkyl-2,2'-bipyridine) complexes of the metal M,
mono(4,4'-dimethoxy-2,2'-bipyridine)bis(4,7-dihydroxy-1,10-phenanthroline) complexes of the metal M,
mono(4,4'-bis(N,N-ethylamino)-2,2'-bipyridine)bis (4,4'-dimethyl-2,2'-bipyridine) complexes of the metal M,
mono(4,4'-bis(N,N-ethylamino)-2,2'-bipyridine)bis (2,2'-bipyridine) complexes of the metal M,
mono(4,4'-bis(N,N-ethylamino)-2,2'-bipyridine)bis (4-alkyl-2,2'-bipyridine) complexes of the metal M,
mono(4,4'-bis(N,N-ethylamino)2,2'-bipyridine) bis (4,7-dihydroxy-1,10-phenanthroline) complexes of the metal M.

When said first ligand ($L_1$, $L_2$) and said second ligand ($L_3$, $L_4$) are different, the preferred mono((ligand L) complexes are the following:
mono(4,4'-dimethoxy-2,2'-bipyridine)mono(4,4'-dihydroxy-2,2'-bipyridine)mono(4,4'-dimethyl2,2'-bipyridine) complexes of the metal M.

The instant invention also provides processes for the preparation of the above-described complexes.

The invention relates in particular to a process for the preparation of a tris (ligand L) complex of a metal M which is iron, ruthenium, osmium or vanadium. The ligand L is a bidentate ligand which is 4,4'-dimethoxy-2,2'-bipyridine, 4,4'-dihydroxy-2,2'-bipyridine or 4,4'-bis(N,N-ethylamino)2,2'-bipyridine.

This process generally comprises:
reacting a soluble salt of the metal M with a substantially stoichiometric amount of a ligand A in the presence of solvents suitable for dissolving this ligand, and then in
refluxing this solution under a nitrogen atmosphere at atmospheric pressure and at a temperature close to the boiling point of these solvents.

DETAILED DESCRIPTION OF THE INVENTION

In the majority of cases, the ligand A is identical to the ligand L or is sufficiently similar thereto to transform into this ligand L during the reaction. The ligand A can, for example, be of the same type as the ligand L, but be differently substituted. This is the case in example 1, where one starts with a bipyridine disubstituted by two methoxy groups to obtain a bipyridine disubstituted by two hydroxy groups. In Example 1, as well as in Examples 5 and 11 described hereinabove 4,4'-dimethoxy-2,2'-bipyridine is used to obtain the complexes with 4,4'-dihydroxy-2,2'-bipyridine since this latter is not commercially available in view of the difficulties and costs of manufacture. The nature of the soluble salt of the metal M varies as a function of the latter. Depending on whether the metal M is iron, ruthenium, osmium or vanadium, the soluble salts are $FeCl_1$, $K_2OsCl_6$, $RuCl_3$ or $VCl_3$ respectively.

The invention primarily relates to a process for the preparation of a tris(4,4-dihydroxy-2,2'-bipyridine) complex of a metal M which is iron, ruthenium, osmium or vanadium.

This process generally comprises:
reacting a soluble salt of the metal M, M being as defined above, with a substantially stoichiometric amount of 4,4'-dimethoxy-2,2'-bipyridine in the presence of ethylene glycol, and then
refluxing this solution under a nitrogen atmosphere at atmospheric pressure and at a temperature of between 190 and 200° C., preferably 195° C.

The soluble salts of the metal M are identical to those described above.

The choice of the solvent used (ethylene glycol) makes it possible to work at elevated temperatures (about 190° to 200° C.) and to only cleave the bond between $OCH_3$ and the bipyridine without any other chemical changes occurring.

Once the $OCH_3$ bond is cleaved, the OH groups are then able to form to yield a tris(4,4'-dihydroxy-2,2'-bipyridine) complex of the metal M.

A specific example for obtaining one of these complexes is given below.

EXAMPLE 1

Preparation of the complex tris(4,4'-dihydroxy-2,2'-bipyridine) osmium 0.100 g (0.21 mmol) of $K_2OsCl_6$ are dissolved in 10 ml ethylene glycol and 0.144 g (0.67 mmol) of 4,4'-dimethoxy-2,2'-bipyridine are added. The solution is refluxed for at least 24 hours under a nitrogen atmosphere at atmospheric pressure and at a temperature between about 190° and 200° C., preferably 195° C. A brown colour appears. After leaving the solution to cool to room temperature it is concentrated to half its original volume. The product is precipitated as its trifluoromethanesulfonate form by adding trifluoromethane sulfonic acid to the ethylene glycol solution.

The complex obtained is filtered, washed with a mixture (1:10 vol/vol) of acetone and diethyl ether and then dried under a high vacuum.

Tris(4,4'-dimethoxy-2,2'-bipyridine) osmium is obtained having the following physico-chemical properties:

Elementary analysis

Formula: $C_{32}H_{24}N_6O_{12}F_6OsS_2$ (1.55 $H_2O$) (measurements made with the trifluromethanesulfonate)

|        | Calculated | Found  |
|--------|------------|--------|
| C      | 35.56%     | 35.75% |
| H      | 2.53%      | 3.02%  |
| N      | 7.78%      | 7.10%  |
| $H_2O$ | 2.58%      | 2.58%  |

Oxidation-reduction potential E° (normal potential)

When the complex is dissolved in an organic solvent such as acetonitrile in the presence of $LiCl_4$ 0.2M, and a potentiodynamic measurement is carried out using a vitreous carbon electrode, one obtains E°= +280 mV (in relation to a calomel reference electrode SCE).

In an aqueous solvent: PBS (phosphate buffer solution: NaCl 100 mM, $NaH_2PO_4$ 10 mM, first adjusted to pH 7.4 then to pH 1 and then to pH 13) with a carbon electrode, one obtains:
pH=1 E°= +150 mV (SCE)
pH=13 E°= −1 V (SCE)

NMR

The sample dissolved in $CD_2Cl_2$ displays no $OCH_3$ peak at 4.1 ppm which indicates that these groups are completely hydrolysed to form OH groups. Aromatic proton peaks are observed between 6.8 ppm and 8 ppm in relation to a tetramethylsilane standard.

Absorption spectrum data of UV and visible waves

| wavelength λ max (nm) | extinction coefficient ε ($M^{-1}$ $cm^{-1}$) |
|-----------------------|------------------------------------------------|
| 239                   | 13850                                          |
| 269                   | 13300                                          |
| 300                   | 12600                                          |
| 357                   | 11500                                          |
| 385                   | 10858                                          |
| 474                   | 7430                                           |
| 512                   | 6240                                           |
| 654                   | 1475                                           |
| 712                   | 1156                                           |

When the ligand L is 4,4'-dimethoxy-2,2'-bipyridine, the process for the preparation of the tris (ligand L) complex of metal M comprises:
 reacting a soluble salt of the metal M with a substantially stoichiometric amount of 4,4'-dimethoxy-2,2'-bipyridine in the presence of methanol, of DMF (dimethylformamide) and/or water, and then
 refluxing this solution under a nitrogen atmosphere at atmospheric pressure and at a temperature between about 70° and 80° C.

The choice of the solvents used (methanol, DMF and/or water) is important because it makes it possible, unlike in Example 1, to work at relatively low temperatures (about 70° to 80° C.) and thereby avoid cleavage of the bond between the $OCH_3$ group and the bipyridine. In addition, these solvents make it possible to reduce the metal M from a +3 oxidation state to a +2 state for ruthenium, from a +4 state to a +2 state for osmium and from a +3 state to a +2 state for vanadium. Iron does not change the oxidation state, being already in the +2 oxidation state. Nonetheless it will be noted that for the vanadium it is necessary to use additional reagents to reach the desired 0 oxidation state A specific example for obtaining one of these complexes is given below.

EXAMPLE 2

Preparation of the complex tris(4,4'-dimethoxy-2,2'-bipyridine) osmium.

0.100 g (0.21 mmol) of $K_2OsCl_6$ is dissolved in a mixture of 5 ml of water, 5 ml of methanol and 5 ml of DMF. 0.144 g (0.67 mmol) of 4,4'-dimethoxy-2,2'-bipyridine are added to this solution and the mixture is refluxed for at least 60 hours under a nitrogen atmosphere at atmospheric pressure and at a temperature between about 70° and 80° C.

A brown colour appears. After cooling to the room temperature the solution is filtered and the solvent is completely eliminated by rotary evaporation. A minimum of ethanol is then added to dissolve the product and the solution is then filtered to remove the insoluble KCl. The product is then precipitated in the form of the trifluoromethanesulfonate by addition of dilute trifluoromethanesulfonic acid. The complex is then filtered, washed with a 1:10 vol/vol mixture of acetone and diethylether and then dried under a high vacuum.

A tris(4,4'-dimethoxy-2,2'-bipyridine) osmium complex is then formed with the following physico-chemical properties:

Elementary analysis

Formula: $C_{38}H_{36}N_6O_{12}F_6OsS_2$ (1.11 $H_2O$) (measurements made with the trifluromethanesulfonate)

|        | Calculated | Found  |
|--------|------------|--------|
| C      | 39.45%     | 39.13% |
| H      | 3.33%      | 3.27%  |
| N      | 7.26%      | 7.41%  |
| $H_2O$ | 1.73%      | 1.73%  |

Oxidation-reduction potential E° (normal potential)

When the complex is dissolved in an organic solvent such as acetonitrile in the presence of $LiCl_4$ 0.2M, and a potentiodynamic measurement is carried out using a vitreous carbon electrode, one obtains E°= +325 mV in relation to a calomel reference electrode (SCE).

In an aqueous solvent: PBS (phosphate buffer solution: NaCl 100 mM, $NaH_2PO_4$ 10 mM, first adjusted to pH 7.4) with a carbon electrode, one obtains E°= +225 mV.

NMR

The sample dissolved in $CD_2Cl_2$ displays a $OCH_3$ peak at 4.1 ppm and aromatic proton peaks between 6.8 ppm and 8.0 ppm in relation to a tetramethylsilane standard.

Absorption Spectrum data of UV and visible waves

| wavelength λ max (nm) | extinction coefficient ε ($M^{-1}$ $cm^{-1}$) |
|-----------------------|------------------------------------------------|
| 228                   | 80800                                          |
| 271                   | 70800                                          |
| 333                   | 22236                                          |
| 385                   | 16012                                          |
| 397                   | 15296                                          |
| 470                   | 12564                                          |

-continued

| wavelength λ max (nm) | extinction coefficient ε (M$^{-1}$ cm$^{-1}$) |
|---|---|
| 510 | 11404 |
| 630 | 4820 |
| 696 | 4012 |

The general process for preparing a tris(4,4'-bis(N,N-ethylamino)-2,2'-bipyridine) complex of a metal M which is iron, ruthenium, osmium or vanadium will now be described.

This process comprises:

reacting a soluble salt of the metal M with a substantially stoichiometric amount of 4,4'-bis(N,N-ethylamino)-2,2'-bipyridine in the presence of ethylene glycol and then refluxing this solution under a nitrogen atmosphere at atmospheric pressure and at a temperature between about 190° and 200° C., preferably 195° C.

The soluble salt of the metal M is identical to those previously described.

A specific example for obtaining one of these complexes is given below.

EXAMPLE 3

Preparation of the Complex tris(N,N-ethylamino)-2,2'-bipyridine) osmium 0.100 g (0.21 mmol) of K$_2$OsCl$_6$ is dissolved in 10 ml of ethylene glycol and 0.193 g (0.64 mmol) of 4,4'-bis(N,N-ethylamino)-2,2'-bipyridine are added. This solution is refluxed for at least 10 hours under a nitrogen atmosphere at atmospheric pressure and at a temperature between about 190° and 200° C., preferably at 195° C. After allowing the solution to cool to room temperature it is filtered and the solvent is concentrated to half its original volume. The product is precipitated in the form of the trifluoromethanesulfonate by adding trifluoromethanesulfonic acid.

The complex obtained is filtered, washed with a mixture (1:10 vol/vol) of acetone and diethylether and dried under a high vacuum.

The instant invention also relates to the preparation of the bis (ligand L) mono (ligand B) complex of a metal M which is iron, osmium, ruthenium or vanadium, the ligand L being 4,4'-dimethoxy-2,2'-bipyridine; 4,4'-dihydroxy-2,2'-bipyridine or 4,4'-bis(N,N-ethylamino)-2,2'-bipyridine) and the ligand B being a bidentate ligand such as those referred to at the beginning of the specification.

One embodiment of this complex (bis ligand L) Cl$_2$ of a said metal M will now be described. It is, however, obvious that the bis (ligand L) Cl$_2$ complex of the metal M used in the preparation of the bis (ligand L) mono (ligand B) complex of the metal M does not necessarily have to be prepared as described herein.

The preparation of the bis (ligand L) Cl$_2$ complex of a metal M which is iron, osmium, ruthenium or vanadium, the ligand L being 4,4'-dimethoxy-2,2'-bipyridine or 4,4'-dihydroxy-2,2'-bipyridine generally comprises:

reacting a soluble salt of the metal M (M being as described above) with a substantially stoichiometric amount of 4,4'-dimethoxy-2,2'-bipyridine in the presence of an appropriate mixture of solvents, especially for example water and methanol in the case of the first ligand L and ethylene glycol in the second case, and then refluxing this solution under a nitrogen atmosphere at atmospheric pressure and for example at a temperature between 70° and 80° C. if water and methanol is used or at a temperature between 190° and 200° C. if ethylene glycol is used.

The preparation of this same complex when the ligand L is 4,4'-bis(N,N-ethylamino)-2,2'-bipyridine generally comprises:

reacting a soluble salt of the metal M, M being as defined above, with a substantially stoichiometric amount of 4,4'-bis(N,N-ethylamino)-2,2'-bipyridine in the presence of DMF and then refluxing this solution under a nitrogen atmosphere at atmospheric pressure and at a temperature between 150° and 155° C.

In these two cases, the soluble salts of the metal M are those described earlier.

Three more specific examples of preparation are given below.

EXAMPLE 4

Preparation of the complex bis(4,4'-dimethoxy-2,2'-bipyridine) osmium 0.100 g (0.21 mmol) of K$_2$OsCl$_6$ are dissolved in a mixture of 5 ml of water and 5 ml of methanol and 0.90 g (0.42 mmol) of 4,4'-dimethoxy-2,2'-bipyridine are added to the solution. The solution is refluxed for at least 2 hours under a nitrogen atmosphere at atmospheric pressure and at a temperature between 70° and 80° C. A dark violet colour appears. The solution is allowed to cool to room temperature and the solvent is completely removed by rotary evaporation. 10 ml of water are then added. The bis(4,4'-dimethoxy-2,2'-bipyridine) Cl$_2$ osmium complex is then isolated by filtration, washed with water and then with a mixture of acetone and diethylether (1:6 vol/vol) to eliminate traces of unreacted ligand. Finally, this complex is dried under a high vacuum.

The results of the elementary analysis are given below.

Elementary analysis

Formula: C$_{24}$H$_{24}$N$_4$O$_4$OsCl$_2$

| | Calculated | Found |
|---|---|---|
| C | 41.56% | 42.02% |
| H | 3.49% | 3.73% |
| N | 8.08% | 8.45% |

EXAMPLE 5

Preparation of a bis(4,4'-dihydroxy-2,2'-bipyridine) Cl$_2$ osmium complex 0.100 g (0.21 mmol) of K$_2$OsCl$_6$ are dissolved in a mixture of 2 ml of water and 10 ml of ethylene glycol and 0.090 g (0.42 mmol) of 4,4'-dimethoxy-2,2'-bipyridine are added to the solution. The solution is refluxed for at least 16 hours under a nitrogen atmosphere at atmospheric pressure and at a temperature between 190° and 200° C., preferably 195° C. A dark violet colour appears. The solution is cooled to room temperature and then concentrated by rotary evaporation. The product obtained is precipitated by addition of acetone. The precipitate is isolated by filtration, washed with acetone and ether and then dried under a high vacuum.

The bis(4,4'-dihydroxy-2,2'-bipyridine) Cl₂ osmium complex obtained in this manner takes the form of blue crystals. The yield is 80 to 90%.

In these two Examples 4 and 5, the choice of solvents and the reaction temperatures were governed by the same rationale as that previously referred to.

EXAMPLE 6

Preparation of the complex bis(4,4'-bis(N,N-ethylamino)-2,2'-bipyridine Cl₂ osmium 0.100 g (0.21 mmol) of $K_2OsCl_6$ are dissolved in 10 ml DMF and 0.125 g (0.42 mmol) of 4,4'-bis(N,N-ethylamino)2,2'-bipyridine are added to the solution.

The solution is refluxed for at least 4 hours under a nitrogen atmosphere at atmospheric pressure and at a temperature between 150° and 155° C. The solution is allowed to cool to the room temperature and the solvent is completely removed by rotary evaporation. 10 ml of cold water are added and the complex bis(4,4'-bis(N,N-ethylamino)-2,2'-bipyridine) Cl₂ osmium (which is poorly soluble) is isolated by filtration. This complex is then washed with cold water and then with a mixture (1:6 vol/vol) of acetone and diethylether to remove trace of unreacted ligand and then dried under high vacuum.

The preparation of the bis (ligand L) mono ((ligand B) complex of a metal M, previously referred to will now be described.

This process comprises:

reacting a bis (ligand L) Cl₂ complex of said metal M with a substantially stoichiometric amount of the ligand B in the presence of suitable solvents to dissolve this complex and the ligand B and then refluxing the solution under a nitrogen atmosphere at atmospheric pressure and at a temperature around the boiling point of these solvents.

As previously mentioned, if the ligand B is 4,4'-dihydroxy-2,2'-bipyridine the chlorinated complex is preferably reacted with 4,4'-dimethoxy-2,2'-bipyridine because this is readily available on the market.

Three more specific embodiments will now be described.

EXAMPLE 7

Preparation of the complex bis(4,4'-dimethoxy-2,2'-bipyridine) mono(4,4'-dimethyl2,2'-bipyridine) osmium 0.05 g (0.07 mmol) of a bis(4,4'-dimethoxy-2,2'-bipyridine) Cl₂ osmium complex are reacted with 0.017 g (0.09 mmol) 4,4'-dimethyl-2,2'-bipyridine in the presence of a mixture of 10 ml of DMF (dimethylformamide), 10 ml water and 10 ml methanol. The mixture is refluxed for at least 40 hours under a nitrogen atmosphere at atmospheric pressure and at a temperature between 70° and 80° C. Finally, the reaction mixture is allowed to cool to the room temperature, is filtered and the solvent is completely removed by rotary evaporation. The product is then dissolved in a minimum of ethanol and precipitated in the form of the trifluoromethanesulfonate by adding trifluoromethanesulfonic acid. Finally, the precipitate is filtered, washed with a mixture of acetone and diethylether (1:6 vol/vol) and dried under high vacuum.

Elementary analysis

Formula: $C_{38}H_{36}N_6O_{10}F_6OsS_2$ (measurements made (0.90 H₂O) with the trifluromethanesulfonate)

|   | Calculated | Found |
|---|---|---|
| C | 40.71% | 41.03% |
| H | 3.40% | 3.46% |
| N | 7.5% | 7.58% |
| F | 10.17% | 10.24% |
| H₂O | 1.45% | 1.44% |

Oxidation-reduction potential E° (normal potential)

When the complex is dissolved in an organic solvent such as acetonitrile in the presence of LiClO₄ 0.2M and a potentiodynamic measurement is effected using a vitreous carbon electrode one obtains E° = +450 mV (reference: calomel electrode SCE). In a phosphate buffer PBS (NaCl 100 mM, NaH₂ PO₄ 10 mM adjusted to pH 7.4), with a vitreous carbon electrode one obtains E° = +340 mV (reference: calomel electrode SCE).

NMR

The sample dissolved in CD₂Cl₂ gives a peak for OCH₃ at 4.1 ppm and a peak for CH₃ at 2.65 ppm as well as aromatic proton peaks between 6.8 ppm and 8.0 ppm in relation to a tetramethylsilane standard.

Absorption spectrum data of the UV and visible waves

| wavelength λ max (nm) | extinction coefficient $\epsilon$ (M⁻¹ cm⁻¹) |
|---|---|
| 216 | 108000 |
| 290 | 62000 |
| 336 | 15520 |
| 378 | 14580 |
| 462 | 13528 |
| 494 | 13376 |
| 628 | 6920 |
| 674 | 6540 |

EXAMPLE 8

Preparation of the complex bis(4,4'-dihydroxy-2,2'-bipyridine) mono(4,4'-dimethyl-2,2'-bipyridine) osmium.

0.05 g (0.07 mmol) of bis(4,4'-dihydroxy-2,2'-bipyridine) Cl₂ osmium complex is reacted with 0.017 g (0.09 mmol) of 4,4'-dimethyl-2,2'-bipyridine in 10 ml ethylene glycol, the mixture is refluxed for at least 4 hours under a nitrogen atmosphere at atmospheric pressure and at a temperature between 190° and 200° C., preferably 195° C. A brown colour appears. The reaction mixture is cooled to room temperature and then the solvent is concentrated to half its original volume. The product obtained is precipitated in the form of the trifluoromethanesulfonate by addition of dilute trifluoromethanesulfonic acid to the ethylene glycol solution. The bis(4,4'-dihydroxy-2,2'-bipyridine) mono(4,4'-dimethyl-2,2'-bipyridine) osmium complex obtained is filtered, washed with a mixture of acetone and diethylether (1:10 vol/vol) and dried under a high vacuum.

EXAMPLE 9

Preparation of the complex bis(4,4'-bis(N,N-ethylamino)-2,2'-bipyridine) mono(4,4'-dimethyl-2,2'-bipyridine) osmium 0.05 mg (0.058 mmol) of bis(4,4'-bis-(N,N-ethylamino)-2,2'-bipyridine) Cl₂ osmium complex is reacted with 0.014 g (0.07 mmol) of 4,4'-dimethyl-2,2'-bipyridine in 10 ml ethylene glycol and this solution is then refluxed for at least 6 hours under a nitrogen atmosphere at atmospheric pressure and at a temperature between 190° and 200° C., preferably at 195° C. The reaction mixture is cooled to room temperature and then filtered and the solvent concentrated to half its original volume. The product obtained is precipitated in the form of the trifluoromethanesulfonate by adding trifluoromethanesulfonic acid. The precipitate is filtered, washed with a mixture (1:6 vol/vol) of acetone and diethylether then dried under high vacuum.

The processes of preparation that have just been described in Examples 7, 8 and 9 for osmium may be generalized to iron, ruthenium and vanadium.

The invention also relates to a process for the preparation of a mono (ligand L) bis (ligand B) complex of a metal M which is iron, osmium, ruthenium or vanadium. As before, the ligand L is 4,4'-dimethoxy-2,2'-bipyridine; 4,4'-dihydroxy-2,2'-bipyridine or 4,4'-bis(N,N-ethylamino)-2,2'-bipyridine and the ligand B is one of the bidentate ligands referred to at the beginning of the specification.

This procedure generally comprises:

reacting a bis (ligand B) $Cl_2$ complex of said metal M with a ligand A in the presence of appropriate solvents to dissolve this complex and the ligand A, the ligand A being chosen in such a way as to transform itself into ligand L during the reaction, in refluxing this solution under a nitrogen atmosphere at atmospheric pressure and at a temperature close to the boiling point of said solvents. As has already been seen, the ligand A is generally identical to the ligand L or is of the same nature as this ligand with different substituents. Example 11 illustrates the latter case for example.

Three more specific embodiments are given below.

EXAMPLE 10

Preparation of the complex
mono((4,4'-dimethoxy-2,2'-bipyridine)bis4,4'-dimethyl-2,2'-bipyridine) osmium.

0.05 g (0.08 mmol) of a bis(4,4'-dimethyl-2,2'-bipyridine) $Cl_2$ osmium complex, the preparation of which is known per se, is reacted with 0.022 g (1.0 mmol) of 4,4'-dimethoxy-2,2'-bipyridine in a mixture of 10 ml of DMF (dimethylformamide), 10 ml of water and 10 mg of methanol. The solution is refluxed for at least 40 hours under a nitrogen atmosphere at atmospheric pressure and at a temperature between 70° and 80° C. The reaction mixture is cooled to the room temperature, filtered and the solvent is completely eliminated by rotary evaporation.

The product is dissolved in a minimum of ethanol and then precipitated in the form of the trifluoromethanesulfonate by addition of trifluoromethanesulfonic acid. The complex obtained in the form of a precipitate is filtered with a mixture of acetone and of diethylether (1:6 vol/vol) and then dried under a high vacuum.

This complex has the following physico-chemical properties:

Oxidation-reduction E° potential (normal potential)

When the complex is dissolved in an organic solvent such as acetonitrile in the presence of a salt of $LiClO_4$ 0.2M and a potentiodynamic measurement is effected using a vitreous carbon electrode one obtains E° = +500 mV (calomel reference electrode SCE).

In a phosphate buffer PBS (NaCl 100 mM, $NaH_2PO_4$ 10 mM adjusted to pH 7.4) with a vitreous carbon electrode one obtains E°=+390 mV (calomel reference electrode SCE).

Absorption spectrum data of the UV and visible waves

| wavelength $\lambda$ max (nm) | extinction coefficient $\epsilon$ ($M^{-1} cm^{-1}$) |
|---|---|
| 222 | 70248 |
| 290 | 61806 |
| 340 | 13919 |
| 380 | 13884 |
| 452 | 12113 |
| 498 | 12119 |
| 624 | 4763 |
| 684 | 4061 |

EXAMPLE 11

Preparation of the complex
meno(4,4'-dihydroxy-2,2'-bipyridine)bis(4,4'-dimethyl-2,2'-bipyridine) osmium, The process is similar to that described in Example 10 except that 0.05 g (0.08 mmol) of bis(4,4'-dimethyl-2,2'-bipyrindine) $Cl_2$ osmium complex is reacted with 0.0195 g (0.09 mmol) of 4,4'-dimethoxy-2,2'-bipyridine in 10 ml of ethylene glycol and that the mixture is refluxed under a nitrogen atmosphere for at least 16 hours at atmospheric pressure and at a temperature between 190° and 200° C., preferably 195° C.

EXAMPLE 12

Preparation of the complex
mono((4,4'-bis(N,N-ethylamino)-2,2'-bipyridine)-bis(4,4'-dimethyl-2,2'-bipyridine) osmium.

0.05 g (0.08 mmol) of a bis(4,4'-dimethyl-2,2'-bipyridine) $Cl_2$ osmium complex, the preparation of which is known per se, is reacted with 0.026 g (0.08 mmol) of 4,4'-bis(N,N-ethylamino)-2,2'-bipyridine in 10 ml of ethylene glycol. The solution is refluxed for at least 6 hours under a nitrogen atmosphere at atmospheric pressure and at a temperature between 190° and 200° C., preferably 195° C. The reaction mixture is cooled to the room temperature, filtered and the solvent is concentrated to half its original volume. The product is precipitated in the form of the trifluromethanesulfonate by addition of dilute trifluoromethanesulfonic acid. The precipitate obtained is filtered, washed with a mixture (1:6 vol/vol) of acetone and diethylether and then dried under a high vacuum.

The description given in Examples 10, 11 and 12 for osmium can be generalized to iron, ruthenium and vanadium.

In examples 1 to 3 and 7 to 12 the final product is isolated by addition of trifluoromethanesulfonic acid. Nonetheless it is obvious that other salts could be obtained by selecting the appropriate reagents. It would thus be possible to obtain hexafluorophosphates by addition of potassium hexafluorophosphate. In the case of osmium and the use of $K_2OsCl_6$ as starting substance, chlorides could be obtained by adding diethylether.

EXAMPLE 13

Preparation of the complex tris
(4,4'-diamino-2,2'-bipyridine) ruthenium 0,1 g (0,38mmol) of 4,4'-diamino-2,2'-bipyridine is dissolved. This solution is refluxed at least 4 hours under a nitrogen atmosphere at atmospheric pressure and at a temperature between 190° and 200° C., preferably 195° C. After cooling to room temperature 5 ml of acetone and 20 ml of diethylether are added. Then the ether is separated and removed. 20 ml of ether are added anew and the processes is renewed until the complex precipitate. This complex is separated by filtration, washed with ether and dried under high vacuum.

Oxidation-reduction potential E° (normal potential)

When the complex is dissolved in an organic solvent such as acetonitrile in the presence of $LiClO_4$ 0.2M and a potentiodynamic measurement is effected using a vitreous carbon electrode one obtains E°=+450 mV (reference: calomel electrode SEC). In a phosphate buffer PBS (NaCl 100 mM, $NaH_2PO_4$ 10 mM adjusted to pH 7.4), with a vitreous carbon electrode one obtains E°=170 mV (reference: calomel electrode SCE).

Absorption spectrum date of the UV and visible waves

| wavelength λ max (nm) | extinction coefficient ε $(M^{-1} cm^{-1})$ |
|---|---|
| 354 | 17655 |
| 394 | 11988 |
| 472 | 8064 |
| 514 | 9444 |

EXAMPLE 14

Preparation of the complex tris
(4,4'-diamino-2,2'-bipyridine) iron 0,1 g (0,50 mmol) of Fe $Cl_2.4H_2O$ is dissolved in 10 ml of water. This solution is added dropwise to 10 ml of a boiling solution of ethanol containing 0,29 (1,55 mmol) of 4,4'-diamino-2,2'-bipyridine. A purple-red colour appears. After cooling to room temperature 20 ml of diethylether are added to precipitate the complex. This complex is separated by filtration, washed with a mixture of acetone and diethylether (1:6-vol/vol) and dried under high vacuum.

Oxidation-reduction potential E° (normal potential).

When the complex is dissolved in an organic solvent such as acetonitrile in the presence of $LiClO_4$ 0.2M and a potentiodynamic measurement is effected using a vitreous carbon electrode one obtains E°=225 mV (reference: calomel electrode SCE). In a phosphate buffer PBS (NaClO 100 mM, $NaH_2PO_4$ 10 mM adjusted to pH 7.4), with a vitreous carbon electrode one obtains E°=+70 mV (reference: calomel electrode SCE).

Absorption spectrum data Of UV and visible waves

| wavelength λ max (nm) | extinction coefficient ε $(M^{-1} cm^{-1})$ |
|---|---|
| 252 | 110800 |
| 366 | 24800 |
| 494 | 7780 |
| 580 | 10600 |

What is claimed is:

1. A mono, bis or tris (4,4'substituted 2,2'-bipyridine) complex of a metal M having the following formula (I)

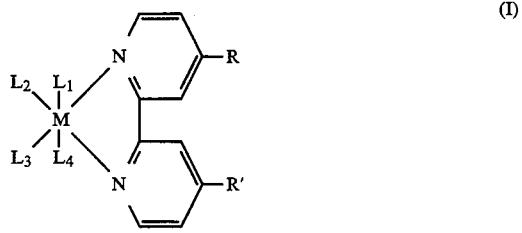

in which M represents iron, ruthenium, osmium or vanadium, R and R' are the same and each is a hydroxy or alkoxy group, or a primary, secondary or tertiary amine group, and $L_{1'}$, $L_{2'}$, $L_3$ and $L_4$ are ligands forming a coordination complex with the metal M, said ligands being a monodentate or being combined together as a didentate, terdentate or tetradentate.

2. A complex according to claim 1 wherein R and R' each represents a hydroxy group, the complex then having the formula (II)

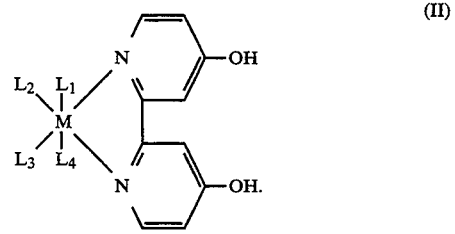

3. A complex according to claim 1 wherein R and R' each represents a methoxy group, the complex then having the formula (III)

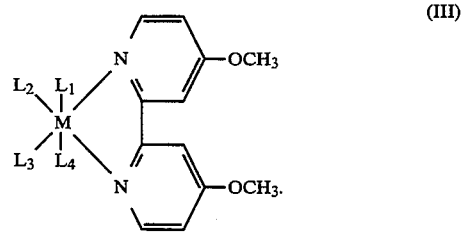

4. A complex according to claim 1 wherein R and R' each represents a N,N-diethylamino group, the complex then having the formula (IV)

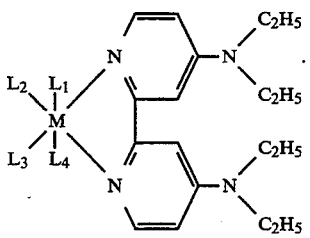

5. A complex according to claim 1 where $L_1$ and $L_2$ together form a bidentate ligand which is ethylenediamine, 1,2-bis(2-pyridyl)ethane, oxalic acid, acetylacetone, glycine or a bipyridine or phenanthroline disubstituted by an $R_1$ group and an $R_2$ group, $R_1$ and $R_2$ being the same or different and each representing hydrogen, $NO_2$, Cl, an alkyl group, an OH group, an alkoxy group, or a primary, secondary or tertiary amine group, and where $L_3$ and $L_4$ are the same or different and each represent a monodentate ligand which is $CN^-$, $Cl^-$, $Br^-$, $I^-$, $SCN^-$, $H_2O$, $NH_3$, triphenylphosphine, trialkylphosphines, primary, secondary or tertiary amines, or pyridine or pyridines substituted by Cl, $NH_2$', $NO_2$ or an alkyl group.

6. A complex according to claim 5 wherein $L_1$ and $L_2$ form a ligand identical to the 4,4'substituted 2,2'-bipyridine moiety and wherein $L_3$ and $L_4$ are each $Cl^-$.

7. A complex according to claim 1 wherein $L_1$ and $L_2$ together on the one hand and $L_3$ and $L_4$ together on the other hand respectively form a bidentate ligand, these two bidentate ligands being the same or different and being ethylenediamine, 1,2-bis(2-pyridyl)ethane, oxalic acid, acetylacetone, glycine, or a bipyridine or phenanthroline disubstituted by an $R_1$ group and an $R_2$ group, $R_1$ and $R_2$ being the same or different and each representing hydrogen, $NO_2$', Cl, an alkyl group, an OH group, an alkoxy group, or a primary, secondary or tertiary amine group.

8. A complex according to claim 7 which is a tris(4,4'-dihydroxy-2,2'-bipyridine) complex of the metal M, a tris(4,4'-dimethoxy-2,2'-bipyridine) complex of the metal M or a tris(4,4'-bis(N,N-ethylamino)-2,2'-bipyridine) complex of the metal M.

9. A complex according to the claim 2 wherein $L_1$ and $L_2$ together form 4,4'-dihydroxy-2,2'-bipyridine and where $L_3$ and $L_4$ together form a bidentate ligand which is ethylenediamine, 1,2-bis(2-pyridyl)ethane, oxalic acid, acetylacetone, glycine, or a bipyridine or phenanthroline disubstituted by an $R_1$ group and an $R_2$ group, $R_1$ and $R_2$ being the same or different and each representing hydrogen, $NO_2$', Cl, an alkyl group, an OH group, an alkoxy group, or a primary, secondary or tertiary amino group.

10. A complex according to claim 9 which is a bis(4,4'-dihydroxy-2,2'-bipyridine)mono(2,2'-bipyridine) complex of the metal M, a bis(4,4'-dihydroxy-2,2'∼-bipyridine)mono(4,4'-dimethoxy-2,2'-bipyridine) complex of the metal M, a bis(4,4'-dihydroxy-2,2'-bipyridine)mono(4,4'-dimethyl-2,2'-bipyridine) complex of the metal M, a bis(4,4'-dihydroxy-2,2'-bipyridine) mono(4-alkyl-2,2'- bipyridine) complex of the metal M, a bis(4,4'-dihydroxy-2,2-bipyridine) mono(4,4'-dialkyl-2,2'-bipyridine) complex of the metal M, a bis(4,4'-dihydroxy2,2'-bipyridine) mono(4,7-dihydroxy-1,10-phenanthroline) complex of the metal M, a bis(4,4'-dihydroxy-1,10-phenanthroline) complex of the metal M, or a bis(4,4'-dihydroxy-2,2'-bipyridine) mono(4,4'-bis(N,N-ethylamino)-2,2'-bipyridine) complex of the metal M.

11. A complex according to the claim 3 where $L_1$ and $L_2$ together form 4,4'-dimethoxy-2,2'-bipyridine and $L_3$ and $L_4$ together form a bidentate ligand which is ethylenediamine, 1,2-bis(2-pyridyl)ethane, oxalic acid, acetylacetone, glycine, or a bipyridine or phenanthroline disubstituted by an $R_1$ group and an $R_2$ group, $R_1$ and $R_2$ being the same or different and each representing hydrogen, $NO_2$, Cl, an alkyl group, an OH group, an alkoxy group, or a primary, secondary or tertiary amine group.

12. A complex according to claim 11 which is a bis(4,4'dimethoxy-2,2'-bipyridine)mono(2,2'-bipyridine) complex of the metal M; a bis(4,4'-dimethoxy-2,2'-bipyridine) mono(4,4'-dimethyl-2,2'-bipyridine) complex of the metal M; a bis(4,4'-dimethoxy-2,2'-bipyridine)mono(4-alkyl-2,2'bipyridine) complex of the metal M; a bis(4,4'-dimethoxy-2,2'-bipyridine)-mono(4,4'-dialkyl-2,2'-bipyridine) complex of the metal M; a bis(4,4'-dimethoxy-2,2'-bipyridine)mono (4,7-dihydroxy-1,10-phenanthroline) complex of the metal M; a bis(4,4'-dimethoxy-2,2'-bipyridine)mono(4,4'-dihydroxy-2,2'-bipyridine) complex of the metal M; or a bis(4,4'-dimethoxy-2,2'-bipyridine)mono(4,4'-bis(N,N-ethylamino)-2,2 -bipyridine) complex of the metal M.

13. A complex according to the claim 4 wherein $L_1$ and $L_2$ together form 4,4'-bis(N,N-ethylamino-2,2'-bipyridine) and where $L_3$ and $L_4$ together form a bidentate ligand which is ethylenediamine, 1,2-bis(2-pyridyl)ethane, oxalic acid, acetylacetone, glycine, or a bipyridine or phenanthroline disubstituted by an $R_1$ group and an $R_2$ group, $R_1$ and $R_2$ being the same or different and each representing hydrogen, $NO_2$, Cl, an alkyl group, an OH group, an alkoxy group, or a primary, secondary or tertiary amino group.

14. A complex according to claim 13 which is bis(4,4'-bis(N,N-ethylamino)-2,2'-bipyridine) mono(2,2'-bipyridine) complex of the metal M; a bis(4,4'-bis(N,N-ethylamino) -2,2'-bipyridine)mono(4,4'-dimethoxy-2,2'-bipyridine) complex of the metal M; a bis(4,4'-bis(N,N-ethylamino-2,2'-bipyridine)mono(4,4'-dimethyl-2,2'-bipyridine) complex of the metal M; a bis(4,4'-bis(N,N-ethylamino)-2,2'-bipyridine) mono(4-alkyl-2,2'-bipyridine) complex of the metal M; a bis(4,4'-bis(N,N-ethylamino)-2,2'-bipyridine)mono( 4,4'-dialkyl-2,2'-bipyridine) complex of the metal M, a bis(4,4'-bis(N,N-ethylamino)-2,2'-bipyridine)mono(4,4'-dihydroxy-2,2'-bipyridine) of the metal M or; a bis(4,4'-bis(N,N-ethylamino)2,2'-bipyridine)mono(4,7-dihydroxy-1,10phenanthroline) complex of the metal M.

15. A complex according to claim 2 wherein $L_1$ and $L_2$ together on the one hand and $L_3$ and $L_4$ together on the other hand respectively form a bidentate ligand, these two ligands being the same and being ethylenediamine, 1,2 bis(2-pyridyl)ethane, oxalic acid, acetylacetone, glycine, or a bipyridine or phenanthroline disubstituted by an $R_1$ group and an $R_2$ group, $R_1$ and $R_2$ being the same or different and each representing hydrogen, $NO_2$, Cl, an alkyl group, an OH group, an alkoxy group, or a primary, secondary or tertiary amino group.

16. A complex according to claim 15 which is a mono(4,4'-dihydroxy-2,2'-bipyridine)bis(4,4'-dimethyl-2,2'-bipyridine) complex of the metal M, a mono(4,4'-dihydroxy-2,2'-bipyridine)bis(2,2'-bipyridine) complex of the metal M, a mono(4,4'-dihydroxy-2,2'-bipyridine)- bis(4-alkyl-2,2'-bipyridine) complex of the metal M, or a mono(4,4'-dihydroxy-2,2'-bipyridine)bis(4,7-dihydroxy-1,10-phenanthroline) complex of the metal M.

17. A complex according to claim 3 wherein $L_1$ and $L_2$ together on the one hand and $L_3$ and $L_4$ together on the other hand respectively form a bidentate ligand, these two bidentate ligands being the same or different and being ethylenediamine, 1,2-bis(2-pyridyl)ethane, oxalic acid, acetylacetone, glycine, or a bipyridine or phenanthroline disubstituted by an R1 group and an $R_2$ group, $R_1$ and $R_2$ being the same or different and each representing hydrogen, $NO_2$, Cl, an alkyl group, an OH group, an alkoxy group, or a primary, secondary or tertiary amine group.

18. A complex according to claim 17 which is a mono(4,4'-dimethoxy-2,2'-bipyridine) bis(4,4'-dimethyl 2,2'-bipyridine) complex of the metal M; a mono(4,4'-dimethoxy-2,2'-bipyridine)bis(2,2'-bipyridine) complex of the metal M, a mono(4,4'-dimethoxy-2,2'-bipyridine)-bis(4-alkyl-2,2'-bipyridine) complex of the metal M; a mono(4,4'-dimethoxy-2,2'-bipyridine) bis(4,7-dihydroxy-1,10-phenanthroline) complex of the metal M; or a mono(4,4'-dimethoxy-2,2'-bipyridine) mono(4,4'-dihydroxy-2,2'-bipyridine)mono(4,4'-dimethyl-2,2'-bipyridine) complex of the metal M.

19. A complex according to the claim 4 wherein $L_1$ and $L_2$ together on the one hand and $L_3$ and $L_4$ together on the other hand respectively form a bidentate ligand, these two bidentate ligands being the same or different and being ethylenediamine, 1,2-bis(2-pyridyl)ethane, oxalic acid, acetylacetone, glycine, or a bipyridine or phenanthroline disubstituted by an $R_1$ group and an $R_2$ group, $R_1$ and $R_2$ being the same or different and each representing hydrogen, $NO_2$, Cl, an alkyl group, an OH group, an alkoxy group, or a primary, secondary or tertiary amine group.

20. A complex according to claim 19 which is a mono(4,4'-bis(N,N-ethylamino)-2,2'-bipyridine) bis(4,4'-dimethyl-2,2'-bipyridine) complex of the metal M; a mono(4,4'-bis(N,N-ethylamino)-2,2'-bipyridine)-bis(2,2'-bipyridine) complex of the metal M; a mono(4,4'-bis(N,N-ethylamino)2,2'-bipyridine) bis(4-alkyl-2,2'-bipyridine) complex of the metal M; or a mono(4,4'-bis(N,N-ethylamino)-2,2 -bipyridine)bis(4,6-dihydroxy-1,10-phenanthroline) complex of the metal M.

21. A complex according to claim 1 wherein the metal M is osmium.

22. A complex according to claim 1 wherein the metal M is ruthenium.

23. A complex according to claim 1 wherein the metal M is iron.

24. A mediator composition for coating an electrode of an amperometric sensor wherein said mediator composition comprises a mono, bis or tris (4,4'substituted 2,2'-bipyridine) complex of a metal M having the following formula (I)

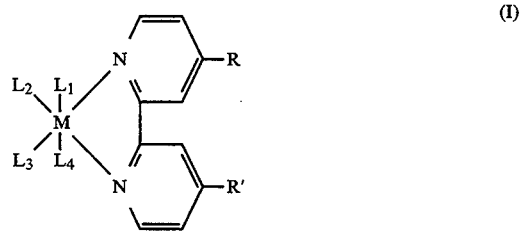

in which M represents iron, ruthenium, osmium or vanadium, R and R' are the same and each is a hydroxy or alkoxy group, or a primary, secondary or tertiary amine group, and $L_{1'}$, $L_{2'}$, $L_3$ and $L_4$ are ligands forming a coordination complex with the metal M, said ligands being a monodentate or being combined together as a didentate, terdentate or tetradentate.

* * * * *